United States Patent [19]

Pappas et al.

[11] Patent Number: 5,462,548
[45] Date of Patent: Oct. 31, 1995

[54] ACETABULAR REAMER

[76] Inventors: Michael J. Pappas, 61 Gould Pl., Caldwell, N.J. 07006; Frederick F. Buechel, 76 Crest Dr., South Orange, N.J. 07079

[21] Appl. No.: 908,963

[22] Filed: Jul. 6, 1992

[51] Int. Cl.[6] .................................. A61B 17/00
[52] U.S. Cl. .................................. 606/80; 606/81
[58] Field of Search ............................. 606/80, 173, 172, 606/179, 180, 181; 408/14, 15, 139, 703; 128/898

[56] References Cited

U.S. PATENT DOCUMENTS

| | | | |
|---|---|---|---|
| 2,525,669 | 10/1950 | Hainault | 606/80 |
| 2,842,131 | 7/1958 | Smith | 606/80 |
| 4,528,980 | 7/1985 | Kenna | 606/80 |
| 4,649,919 | 3/1987 | Thimsen | 606/80 |
| 4,662,891 | 5/1987 | Hoiles | 606/80 |
| 4,706,659 | 11/1987 | Matthews | 606/80 |
| 4,782,833 | 11/1988 | Einhorn | 606/80 |
| 4,803,982 | 2/1989 | Baker | 606/80 |
| 4,856,503 | 8/1989 | Schelhas | 606/80 |
| 4,951,690 | 8/1990 | Baker | 606/80 |
| 5,007,911 | 4/1991 | Baker | 606/80 |

Primary Examiner—Michael A. Brown
Attorney, Agent, or Firm—Anthony J. Casella; Gerald E. Hespos

[57] ABSTRACT

An acetabular reamer is provided with a shaft having opposed front and rear ends. A mounting cap is securely connected to the front end of the shaft and includes a skirt having an interior surface spaced radially outwardly from the shaft and an opposed non-cylindrical exterior surface. At least one aperture extends through the skirt. A locking spring is disposed adjacent the interior surface of the skirt and includes a locking detent extending through the aperture in the skirt. The spring can be deflected radially inwardly to bring the detent into alignment with the exterior surface of the skirt. A reamer head is mountable over the mounting cap such that the rear wall of the reamer head deflects the spring radially inwardly during mounting and unmounting. In the fully mounted condition of the reamer head, the locking detent of the spring engages an inwardly facing surface of the rear wall of the reamer head. The° acetabular reamer further includes a sleeve slidably and rotatably disposed around the shaft. The forward end of the sleeve can be gravitationally advanced into the annular space between the shaft and the skirt to prevent the inward deflection of the spring. Thus, the sleeve and the spring cooperate to prevent unintentional separation of the reamer head from the mounting cap.

11 Claims, 2 Drawing Sheets

ACETABULAR REAMER

BACKGROUND OF THE INVENTION

A prosthetic hip replacement system comprises a femoral component and an acetabular component. The femoral component includes a spherical head which covers or replaces the natural head of the femur. The acetabular components typically include a spherically generated cup which mounts in the acetabular cavity, and a spherically generated liner which mounts in the cup. The spherical head of the femoral component is pivotally engageable in the spherically generated liner of the acetabular component.

Surgery to implant an acetabular component of the prosthetic system requires the surgeon to enlarge and reshape the acetabular cavity in the ilium of the patient. The surgeon is then able to insert the prosthetic cup of the acetabular component into the enlarged and reshaped acetabular cavity.

The surgeon typically uses a prior art acetabular reamer to enlarge and reshape the acetabular cavity of the patient. A typical prior art acetabular reamer includes a reamer head which is a hollow cutting tool with a generally hemispherical front cutting wall, an opposed generally planar rear mounting wall and a hollow bone accumulation cavity therebetween. More particularly, such a prior art reamer head is formed to include a plurality of cutting edges on the hemispherical front cutting wall. These cutting edges are dimensioned to bite into and grate away the bone tissue of the ilium as the reamer head is simultaneous rotated and advanced into the acetabular cavity of the patient. The grated bone tissue accumulates inside the hollow bone accumulation cavity of the reamer head, and the surgeon may subsequently pack the accumulated bone tissue around the prosthetic components to promote bone ingrowth for ensuring a tight fit between the bone and the prosthetic components.

The planar rear mounting wall of such a prior art acetabular reamer includes a non-circular aperture extending centrally therethrough to enable access to the hollow bone accumulation cavity inside the prior art reamer head, and to enable rotatable driving of the reamer head.

The prior art reamer head is used with an elongated prior art reamer shaft having opposed front and rear ends. The rear end is configured and dimensioned for mounting in the chuck of a surgical drill. The front end of the prior art reamer shaft has a non-circular cross-section corresponding to the non-circular aperture in the rear mounting wall of the prior art reamer head. Thus, the reamer head can be frictionally engaged on the front end of the prior art reamer shaft, and may be rotatably driven by the prior art reamer shaft and the surgical drill to prepare the acetabular cavity.

The required detachability between the reamer head and the reamer shaft has been a disadvantage of the prior art acetabular reamer. In particular, the bone tissue of the patient will engage with and exert forces on the cutting edges of the reamer head. The magnitude of these forces may vary from patient to patient depending upon the characteristics of the bone being cut by the reamer head. The surgeon must overcome these forces to withdraw the reamer head from the acetabular cavity. However, the forces exerted by the bone tissue on the cutting edges of the reamer head often exceed the engagement forces between the prior art reamer shaft and the reamer head. In these situations, the reamer shaft will disengage from the reamer head when the surgeon pulls rearwardly on the surgical drill. The surgeon then must use a separate gripping and/or retraction tool to disengage the prior art reamer head from the bone tissue defining the acetabular cavity.

To avoid these problems, some prior art acetabular reamers have included cumbersome latch mechanisms that can be actuated by the surgeon to lock the head to the shaft, and that can be actuated again by the surgeon to enable disengagement of the head. This prior art acetabular reamer latch operation represents a substantial inconvenience to the surgeon.

In view of the above, it is an object of the subject invention to provide an improved acetabular reamer.

It is further an object of the subject invention to provide a reamer head which is securely lockable with the shaft of the acetabular reamer.

It is an additional object of the subject invention to provide a reamer head that is easily disengageable from a reamer shaft.

It is another object of the invention to provide an acetabular reamer with a head that automatically locks to the shaft and automatically unlocks from the shaft during normal usage of the reamer.

SUMMARY OF THE INVENTION

The subject invention is directed to an acetabular reamer with an efficient locking mechanism. The locking mechanism on the acetabular reamer prevents unintended separation of the reamer head from the reamer shaft as the surgeon is withdrawing the reamer head from the acetabular cavity.

The acetabular reamer of the subject invention includes a reamer shaft, a mounting cap, a locking spring, a reamer head and a sleeve. The reamer shaft has opposed front and rear ends. The rear end of the reamer shaft is connectable to a surgical drill substantially as in the prior art. The front end of the reamer shaft rigidly engages a mounting cap with exterior and interior surfaces. The exterior surface is noncylindrical, and may be of hexagonal or octagonal cross-section. The interior surface of the mounting cap is spaced radially outwardly from the shaft. The interior surface of the mounting cap may be generally cylindrical such that a generally annular space exists between the mounting cap and the reamer shaft.

The reamer head includes a generally hemispherical front wall with a plurality of grating or cutting edges for removing bone tissue of the patient. A rear wall of the reamer head has a non-circular aperture which is dimensioned and configured to achieve a detachable friction fit between the reamer head and the mounting cap.

The acetabular reamer of the subject invention further includes a locking spring which is contained within the mounting cap. The locking spring may be in the form of a leaf spring and may include a locking detent on at least one end of the spring. The locking detent is dimensioned and disposed to pass entirely through the radially aligned hole in the mounting cap and to engage a portion of the rear wall of the reamer head within the bone accumulation cavity thereof. In this manner, the locking detent helps to retain the reamer head on the mounting cap. However, a sufficient force exerted on the reamer head will cause the locking spring to be deflected radially inwardly a sufficient distance for the rear wall of the reamer head to pass the detent of the locking spring.

The acetabular reamer of the subject invention further includes a sleeve mounted on the reamer shaft to permit both rotational and axially slidable movement therebetween. The sleeve enables the surgeon to precisely guide the reamer into the acetabular cavity of the patient. The sleeve includes a front end that is dimensioned to be slidably advanced into the annular space between the reamer shaft and the interior surface of the mounting cap. More particularly, the front end of the sleeve is dimensioned to substantially engage against the locking spring and to thereby prevent the radially inward deflection of the locking spring that is required to separate the reamer head from the mounting cap. The sleeve can be moved rearwardly along the reamer shaft and out of the annular space between the shaft and the mounting cap. In this axial orientation, the locking spring can be deflected radially inwardly to enable separation of the reamer head from the mounting cap.

The surgeon can use the acetabular reamer of the subject invention substantially as in the prior art. During this normal usage, the reamer head will be pointed gravitational downwardly and toward the acetabular cavity. Hence, during the entire preparation of the acetabular cavity, the sleeve is retained by gravity in its forward most position. The forward disposition of the sleeve ensures that the locking spring cannot be deflected inwardly. Hence, the locking spring is retained in its locking orientation with the locking detent thereof engaged against the rear wall of the reamer head to prevent separation of the reamer head from the mounting cap as the acetabular reamer is withdrawn by the surgeon. Upon removal of the reamer head from the surgically prepared cavity, the surgeon need merely invert the drill so that the sleeve can slide rearwardly under the action of gravity to enable disengagement of the reamer head from the mounting cap. The surgeon can then remove the bone tissue from the bone accumulation cavity of the reamer head for subsequent use in the surgical procedure as necessary.

DETAILED DESCRIPTION OF THE PREFERRED EMBODIMENT

Figure 9:
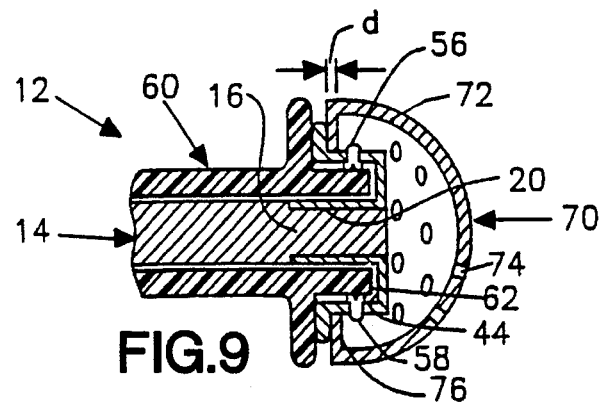
FIG. 9 is a cross-sectional view taken along line 9—9 in FIG. 8.
Figure 10:
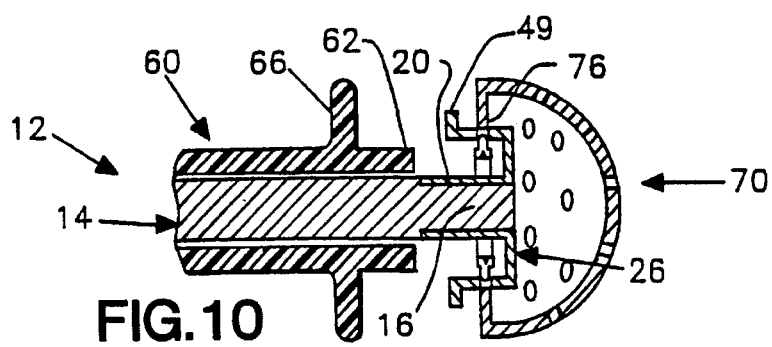
FIG. 10 is a cross-sectional view similar to FIG. 9, but showing the respective components disposed for separation of the reamer head from the mounting cap.

The acetabular reamer of the subject invention is identified generally by the numeral 12 in FIGS. 1–10. The acetabular reamer 12 includes a cylindrical reamer shaft 14 having opposed front and rear ends 16 and 18 respectively. The front end 16 includes an array of external threads 20 as shown in FIGS. 9 and 10. The rear end 18 is connectable to a surgical drill which is illustrated schematically in FIG. 1 and identified generally by the numeral 22. An annular ridge 24 defining a major diameter on the reamer shaft 14 is disposed intermediate the front and rear ends 16 and 18.

Figure 1:
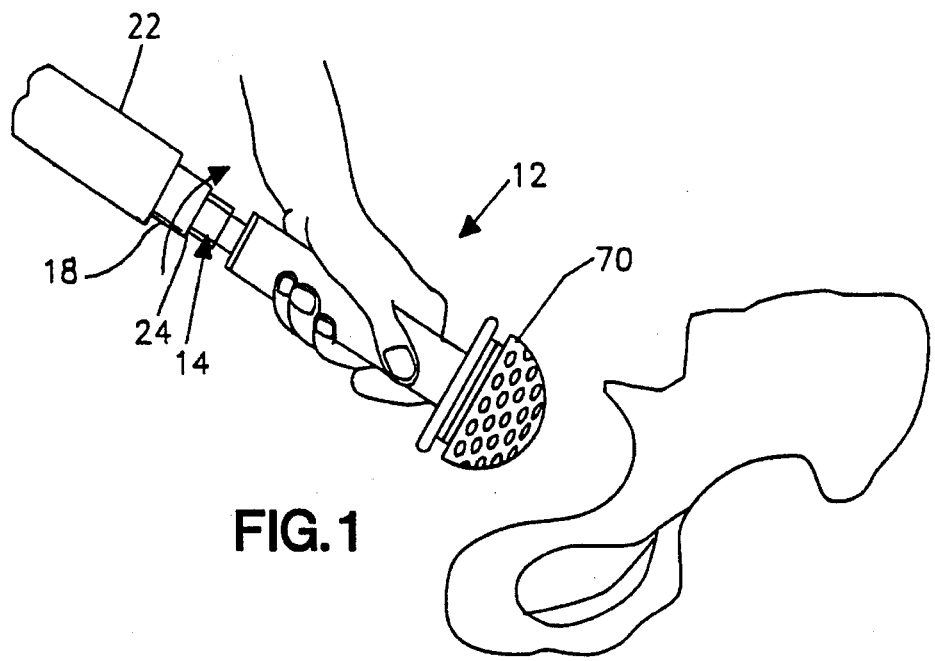
FIG. 1 is a perspective view of an acetabular reamer during surgery.
Figure 2:
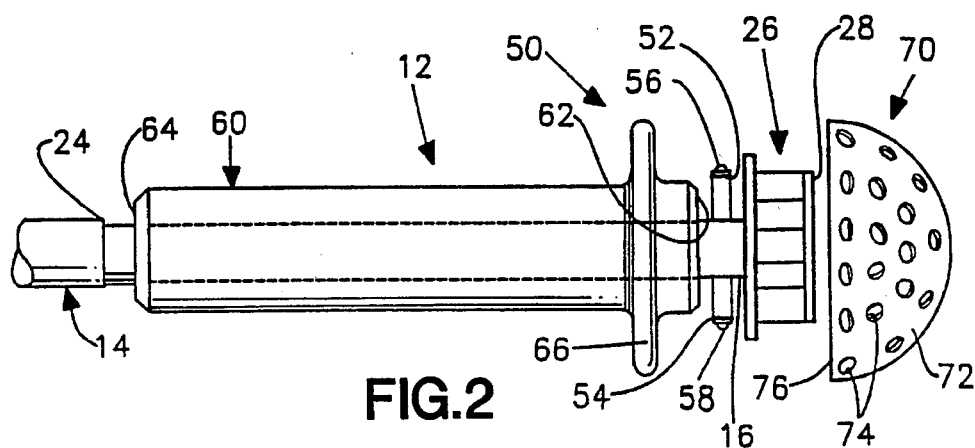
FIG. 2 is an exploded side elevational view of an acetabular reamer.
Figures 3, 4, 5:
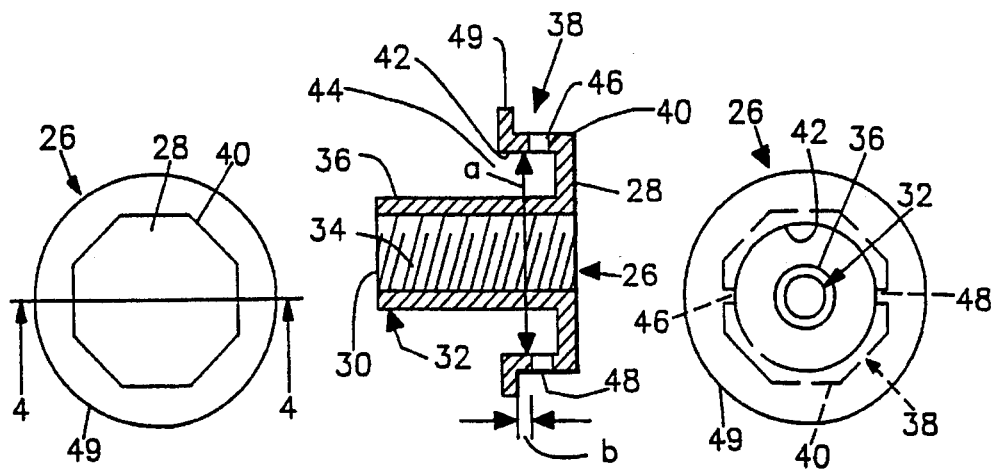
FIG. 3 is a front elevational view of the mounting cap for the acetabular reamer depicted in FIG. 2.
FIG. 4 is a cross-sectional view taken along line 4—4 in FIG. 3.
FIG. 5 is a rear elevational view of the mounting cap.
Figure 6:
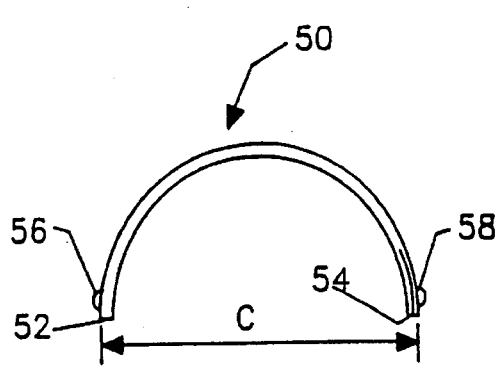
FIG. 6 is a front elevational view of a locking spring for the acetabular reamer.
Figure 7:
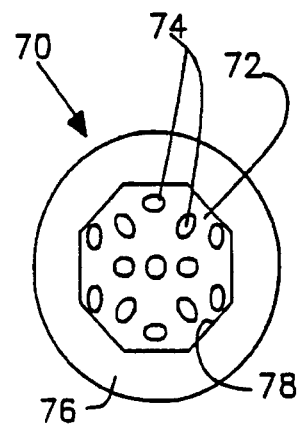
FIG. 7 is a rear elevational view of the reamer head.
Figure 8:
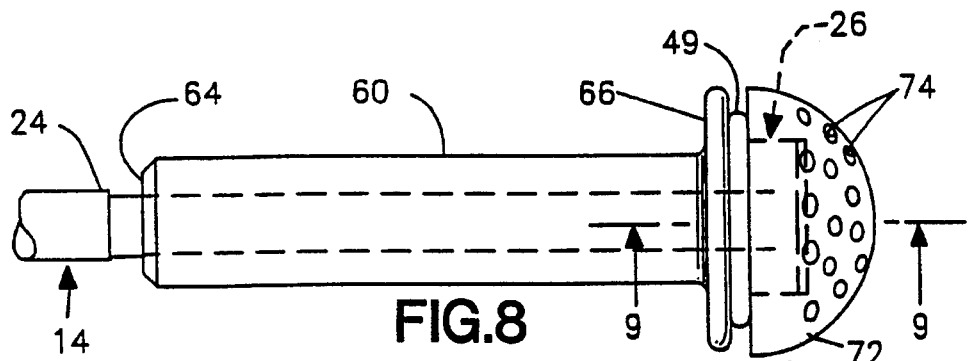
FIG. 8 is a side elevational view of the assembled acetabular reamer.

A mounting cap 26 is engageable with the front end 16 of the reamer shaft 14. The mounting cap 26 includes opposed front and rear ends 28 and 30. The rear end 30 is characterized by an axially aligned mounting tube 32 having an array of internal threads 34 for threaded engagement with the external threads 22 at the front end 16 of the reamer shaft 14. The mounting tube 32 includes a cylindrical exterior surface 36. A mounting skirt 38 extends rearwardly from the front end 28 of the mounting cap 26 and in spaced relationship to the mounting tube 32. The mounting skirt 38 is characterized by an exterior surface 40 of octagonal cross-sectional shape as illustrated most clearly in broken lines in FIG. 5. It is to be understood, however, that other non-cylindrical exterior surfaces would be equally effective. The skirt 38 further includes a cylindrical interior surface 42 which is spaced from the exterior cylindrical surface 36 of the mounting tube 32 and defines a diameter "a" as shown in FIG. 4. With this arrangement, an annular space 44 exists between the tube 32 and the skirt 38.

Diametrically opposed apertures 46 and 48 extend through the skirt 38 from the interior surface 42 to the exterior surface 40. These apertures are used to accommodate locking detents, as explained further herein. The skirt 38 further includes a radially outwardly extending flange 49 at the rearward extreme thereof. The flange 49 is spaced rearwardly from the apertures 46 and 48 by a distance "b" as shown in FIG. 4.

A locking spring 50 is biasingly retained in the annular space 44 between the mounting tube 32 and the mounting skirt 38 of the mounting cap 26. The locking spring is a leaf spring of generally semi-circular shape and defining an outer diameter "c" which, in its unbiased condition, is slightly greater than the diameter "a" of the inner surface 42 of the skirt 38 on the mounting cap 26. The locking spring 50 includes opposed ends 52 and 54. Rounded locking detents 56 and 58 are staked to the spring 50 to extend generally radially outwardly from locations in proximity to the ends 52 and 54 respectively. The locking spring 50 is retained in the annular space 44 between the tube 32 and the skirt 38 of the mounting cap 26. More particularly, the outer diameter "c" of the mounting spring 50 is dimensioned for securely seating against the cylindrical inner surface 42 of the skirt 38. Additionally, the locking detents 56 and 58 are disposed and dimensioned to pass through the apertures 46 and 48 respectively in the skirt 38. As shown most clearly in FIG. 9, the rounded locking detents 56 and 58 are dimensioned to extend beyond the exterior surface 40 of the skirt 38. However, as shown in FIG. 10, the opposed ends 52 and 54 of the spring 50 can be biased radially inwardly so that the detents 56 and 58 do not project beyond the exterior surface 40 of the skirt 38.

The acetabular reamer 12 further includes a sleeve 60 which is slidably and rotatably mounted on the shaft 14 forward of the shoulder 24. The sleeve 60 may be grasped by the surgeon to accurately guide the rotating reamer shaft 14 into a surgical cavity. The sleeve 60 includes a front end 62 and a rear end 64. The shoulder 24 on the reamer shaft 14 is dimensioned to engage the rear end 64 of the sleeve 60 to limit the extent of rearward movement of the sleeve 60 on the reamer shaft 14. The front end 62 of the sleeve 60 defines an external diameter "e" which is smaller than the internal diameter defined by the spring 50 as mounted in the annular space 44 of the mounting cap 26. Thus, the front end 62 of the sleeve 60 can be advanced into the annular space 44 between the tube 32 and the skirt 38 of the mounting cap 26 for disposition intermediate the opposed ends 52 and 54 of the spring 50, as shown in FIG. 9. In this disposition, the front end 62 of the sleeve 60 prevents the radially inward deflection of the ends 52 and 54 of the spring 50. The sleeve 60 further includes a collar 66 in proximity to the front end 62. The collar 66 protects the surgeon's hand from the rotating mounting cap 26.

The acetabular reamer 12 further includes a reamer head 70 having a hemispherical front cutting wall 72 with a plurality of cutting edges 74 thereon. The reamer head 70 further includes a rear mounting wall 76 having an octagonal mounting aperture 78 extending therethrough and into a bone accumulation cavity. The octagonal mounting aperture 78 is dimensioned to frictionally engage the exterior surface 40 of the skirt 38 on the mounting cap 26. The rear wall 76 of the reamer head 70 defines a thickness "d" which is less than the axial distance "b" between the flange 49 and the apertures 46, 48 on the skirt 38 of the mounting cap 26.

In use, the surgeon can orient the drill 22 with the front end 16 of the shaft 14 pointing generally upwardly. The sleeve 60 will thus slide gravitationally rearwardly, such that the front end 62 of the sleeve 60 will be free of the annular space 44 between skirt 38 and the tube 36 of the mounting cap 26.

The rear wall 76 of the reamer head 70 then can be urged rearwardly over the skirt 38 of the mounting cap 26. More particularly, the skirt 38 of the mounting cap 26 is advanced partly into the bone accumulation cavity of the reamer head 70. The rear wall 76 of the reamer head 70 will engage the rounded locking detents 56 and 58 of the locking spring 50, and will cause the opposed ends 52 and 54 of the spring 50 to be deflected radially toward one another. Sufficient deflection of the ends 52 and 54 of the spring 50 will enable the rear wall 76 of the reamer head 70 to pass beyond the locking detents 56 and 58. As the rear wall 76 approaches the flange 49 of the skirt 38 the opposed ends 52 and 54 of the spring 50 will resiliently return toward an undeflected condition such that the locking detents 56 and 58 engage rear wall 76 of the reamer head 70 within the bone accumulation cavity 80.

The surgeon can then invert the drill 22 for use, such that the reamer head 70 is pointing down toward the surgical cavity to be prepared. The sleeve 60 will slide gravitationally forwardly and into the annular space 44 of the mounting cap 28. As noted above, the sleeve 60 prevents the ends 52 and 54 of the spring 50 from being biased inwardly, and hence locks the reamer head 70 to the mounting cap 28. The reamer head 70 will remain locked to the mounting cap 28 as long as the front end 16 of the shaft 14 is pointing gravitationally down. This orientation will exist throughout the surgical preparation of the acetabular cavity, and during removal of the acetabular reamer head 70 from the cavity. The locked retention of the reamer head 70 caused by the gravitational disposition of the sleeve 60 prevents the separation of the reamer head 70 during withdrawal of the reamer 12 from the surgical cavity, as had been a problem in the prior art. Upon removal of the acetabular reamer 12 from the surgical cavity, the surgeon need merely invert the drill 22 to enable the sleeve 60 to slide gravitationally rearwardly from its forward most position to effectively unlock the reamer head 70. The surgeon can then pull the reamer head 70 off the mounting cap 28.

The collar 66 of the sleeve 60 is likely to contact tissue adjacent the surgical cavity. This contact with tissue will help to urge the sleeve 60 forwardly as the drill 22 and shaft 14 are pulled rearwardly and out of the surgical cavity. Thus, in the unusual instance where the drill 22 is not pointing gravitationally downward during a reaming operation, the contact between the collar 66 and tissue will achieve a locking of the reamer head 70 to the mounting cap 28. As still a further failsafe, the surgeon may manually urge the sleeve 60 forwardly to ensure positive locking of the reamer head 70.

In summary, an acetabular reamer is provided with a shaft having a mounting cap at the forward end thereof. The mounting cap includes a tube securely engaged on the shaft and a skirt having a non-circular exterior surface and an opposed interior surface spaced radially outwardly from the tube. A plurality of radially aligned apertures are spaced from the flange and extend throughout the skirt from the exterior surface to the interior surface. A locking spring is disposed in the annular space between the skirt and the tube. The spring includes locking detents which pass entirely through the apertures in the skirt. The acetabular reamer further includes a sleeve slidably and rotatably mounted on the shaft. The forward end of the sleeve is dimensioned to be slidably advanced into the annular space between the tube and the skirt of the mounting cap. The sleeve further is dimensioned to prevent inward deflection of the opposed ends of the spring. A reamer head includes a rear wall with a mounting aperture conforming to the exterior shape of the skirt on the mounting cap. Thus, the rear wall of the reamer head can be slidably advanced over the mounting cap. The opposed ends of the spring will deflect radially inwardly as the rear wall of the reamer head advances axially rearwardly over the skirt of the mounting cap. After sufficient rearward movement of the reamer head on the mounting cap, the spring will resiliently return toward an undeflected condition with the locking detents of the spring engaging the inwardly facing surface of the rear wall on the reamer head. The sleeve will slide gravitationally into its forward position during normal usage of the reamer. Thus, the inward deflection of the spring that is required to separate the reamer head from the mounting cap is prevented during normal usage of reamer and as the reamer is being removed from the surgical cavity. The reamer head can be unlocked by inverting the drill to permit the gravitational rearward movement of the sleeve.

While the invention has been described with respect to a preferred embodiment, it is understood that changes can be made without departing from the scope of the invention as defined by the appended claims.

We claim:

1. A surgical reamer, comprising:
   shaft means for delivering rotatable driving forces;
   reamer means selectively engageable and disengageable with the shaft means; and
   gravitationally responsive locking means mounted to the shaft means for positively locking the reamer means to the shaft means when the surgical reamer is disposed in a first gravitational orientation and for unlocking the reamer means from the shaft means when the surgical reamer is disposed in a second gravitational orientation.

2. A surgical reamer as in claim 1, wherein the locking means comprises a sleeve means slidably mounted to the shaft means for slidable movement toward the reamer means in the first gravitational orientation of the surgical reamer for locking the reamer means to the shaft means, said sleeve means being slidably moveable along the shaft means away from the reamer means in the second gravitational orientation of the surgical reamer for unlocking the reamer means from the shaft means.

3. A surgical reamer as in claim 2, wherein the locking means further comprises at least one deflectable detent biasingly mounted to the shaft means for resiliently retaining the reamer means on the shaft means, the sleeve means being engageable with the deflectable detent in the first gravitational orientation of the surgical reamer for preventing deflection of the detent and thereby positively locking the reamer means to the shaft means, the sleeve means being spaced from the deflectable detent in the second gravitational orientation of the surgical reamer, for enabling deflection of the detent and thereby unlocking the reamer means from the shaft means.

4. A surgical reamer as in claim 1, wherein the shaft means comprises a mounting cap at an end thereof remote from the surgical drill, the reamer means being engageable with the mounting cap, the locking means comprising at least one deflectable detent, such that in an undeflected position said detent secures said reamer means on said mounting cap, and such that in a deflected condition said detent permits separation of said reamer means from the mounting cap of the shaft means, said locking means comprising a sleeve slidably mounted to the shaft means, such that in the first gravitational orientation of the surgical reamer, the sleeve slides toward the mounting cap to prevent deflection of the detent and thereby locking the reamer means to the mounting cap, and such that in the second gravitational orientation of the surgical reamer, the sleeve slides away from the mounting cap to permit deflection of the locking detent and thereby enabling removal of the reamer means from mounting cap.

5. A surgical reamer comprising:

shaft means for delivering rotatable driving forces from a surgical drill, the shaft means comprising a mounting cap at an end thereof remote from the surgical drill;

reamer means selectively engageable and disengageable with the mounting cap of the shaft means; and gravitationally responsive locking means mounted to the shaft means for positively locking the reamer to the shaft means when the surgical reamer is disposed in a first gravitational orientation and for unlocking the reamer means from the shaft means when the surgical reamer is disposed in a second gravitational orientation, the locking means comprising a generally semi-circular leaf spring, a pair of detents mounted at generally diametrically opposed locations on the leaf spring such that in an undeflected condition of said leaf spring, said detents secure said reamer means on said mounting cap, and such that in a deflected condition of said leaf spring, said detents permit separation of said reamer means from the mounting cap of the shaft means, said locking means further comprising a sleeve slidably mounted to the shaft means, such that in the first gravitational orientation of the surgical reamer, the sleeve slides toward the mounting cap to prevent deflection of the leaf spring and thereby locking the reamer means to the mounting cap, and such that in the second gravitational orientation of the surgical reamer, the sleeve slides away from the mounting cap to permit deflection of the leaf spring and thereby enabling removal of the reamer means from the mounting cap.

6. An acetabular reamer comprising:

a shaft having opposing front and rear ends;

a mounting cap rigidly connected to the front end of said shaft, said cap having an axially extending skirt with an interior surface spaced radially from the shaft and an opposed exterior surface, at least one hole extending from the interior surface to the exterior surface;

a locking spring disposed against the interior surface of said skirt, at least one detent on the spring disposed and dimensioned to project through the hole in the skirt and beyond the exterior surface thereof, said spring being deflectable inwardly to move the detent into alignment with the exterior surface of the skirt;

a sleeve slidably and rotatably mounted on the shaft and having opposed front and rear ends, the front end being selectively slidably advanceable between the shaft and the spring for preventing inward deflection of the spring; and a reamer head having a front wall and a rear wall with a non-cylindrical aperture engageable over the exterior surface of the skirt, said rear wall being configured to urge the detent radially inwardly for enabling movement of the rear wall rearwardly past the detent and thereby enabling the spring to resiliently return to a position where the detent engages the rear wall intermediate the front and rear walls of the reamer head, whereby the sleeve is selectively slidably advanceable forwardly for preventing inward deflection of the spring and thereby locking the reamer head to the mounting cap.

7. An acetabular reamer as in claim 6, wherein the skirt of the mounting cap defines opposed front and rear ends, the aperture extending through the skirt intermediate the front and rear ends, an outwardly extending flange disposed at the rear end of the skirt and defining a diametric cross-section greater than the cross-section of aperture in the reamer head.

8. An acetabular reamer as in claim 6, wherein the skirt of the mounting cap includes two holes extending through the skirt at spaced apart locations thereon, the locking spring including two detents projecting through the respective holes in the skirt of the mounting cap.

9. An acetabular reamer as in claim 8, wherein the holes extending through the skirt of the mounting cap are disposed at diametrically opposed locations on the skirt.

10. An acetabular reamer as in claim 6, wherein the locking spring is formed from a flat strip of metal, and wherein the detent is defined by at least one rivet staked to the flat strip of metal.

11. An acetabular reamer as in claim 10, wherein the rivet includes a generally semi-spherical head projecting through the hole in the skirt of the mounting cap.

* * * * *